United States Patent [19]

Failla et al.

[11] Patent Number: 5,501,654
[45] Date of Patent: Mar. 26, 1996

[54] ENDOSCOPIC INSTRUMENT HAVING ARTICULATING ELEMENT

[75] Inventors: Stephen J. Failla, Cincinnati; Michael J. Stokes, Gates Mills; Daniel W. Price, Loveland; Charles M. Rarey, Akron; Bennie Thompson, Cincinnati, all of Ohio

[73] Assignee: Ethicon, Inc., Cincinnati, Ohio

[21] Appl. No.: 291,352

[22] Filed: Aug. 16, 1994

Related U.S. Application Data

[63] Continuation of Ser. No. 92,326, Jul. 15, 1993, abandoned.

[51] Int. Cl.$^6$ .......................... A61B 17/02; A61B 17/28; A61B 17/32
[52] U.S. Cl. .................. 600/204; 600/215; 606/47; 606/170; 606/190; 606/206
[58] Field of Search ..................... 606/205–208, 606/174, 170, 46, 47, 190; 128/20, 751; 600/204, 210, 206, 215

[56] References Cited

U.S. PATENT DOCUMENTS

| | | |
|---|---|---|
| 4,665,906 | 5/1987 | Jervis . |
| 5,067,957 | 11/1991 | Jervis . |
| 5,176,651 | 1/1993 | Allgood et al. . |
| 5,195,506 | 3/1993 | Hulfish .................................... 600/204 |
| 5,195,968 | 3/1993 | Lundquist . |
| 5,217,451 | 6/1993 | Freitas .................................. 606/198 X |
| 5,245,987 | 9/1993 | Redmond et al. ....................... 600/204 |
| 5,254,130 | 10/1993 | Poncet et al. ........................ 606/174 X |
| 5,284,128 | 2/1994 | Hart . |
| 5,352,237 | 10/1994 | Rodak et al. ........................ 600/204 X |
| 5,450,842 | 9/1995 | Tovey et al. ........................ 600/204 X |

FOREIGN PATENT DOCUMENTS

| | | | |
|---|---|---|---|
| 526115 | 2/1993 | European Pat. Off. ............... | 606/205 |
| 3641935 | 6/1987 | Germany ............................... | 606/205 |

OTHER PUBLICATIONS

Brochure of Cabot Medical entitled "Nanicoke Advanced Laparascopic/Thoracoscopic Instruments for the Next Generation of Endoscopic Surgery", undated.
United States Surgical Corporation Brochure, Dated 1992.

*Primary Examiner*—Michael H. Thaler
*Attorney, Agent, or Firm*—Dressler, Goldsmith, Shore & Milnamow, Ltd.

[57] ABSTRACT

An elastically deformable element having multiple stacked strips for articulation in an endoscopic surgical instrument. The deformable element is usable in a variable retractor and an instrument having an articulating housing. The working section of the retractor variably moves from a curved configuration when outside of a sheath to a substantially straightened configuration when inside the sheath.

46 Claims, 6 Drawing Sheets

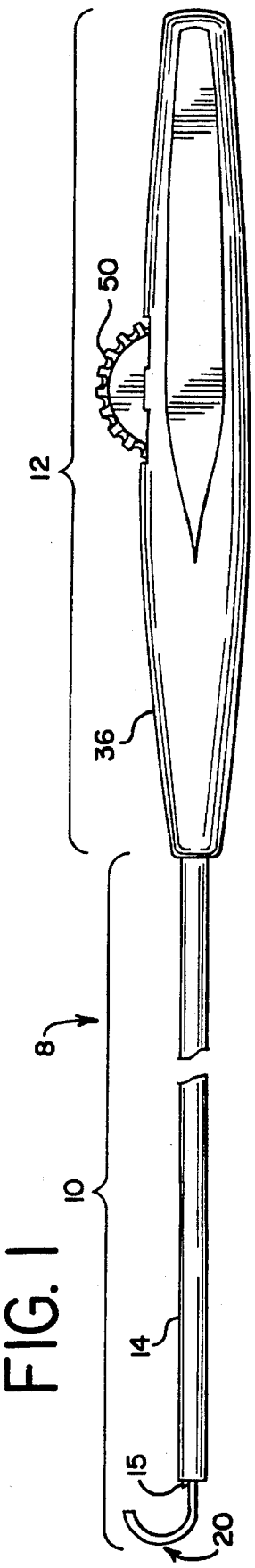
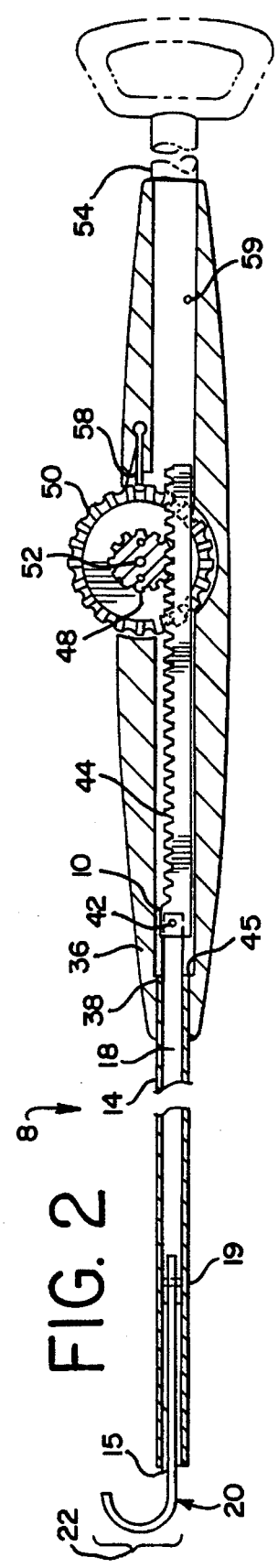
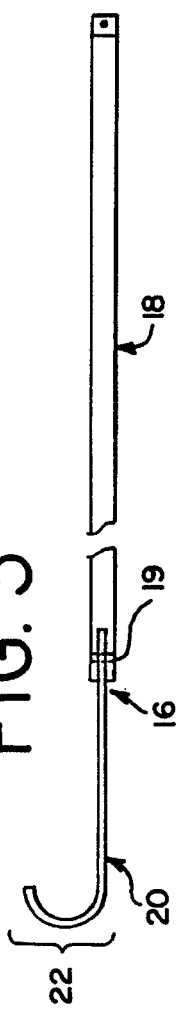

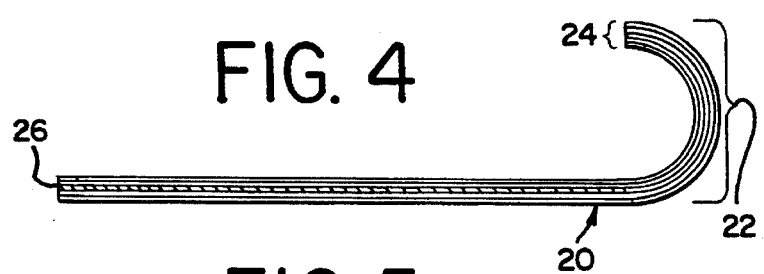
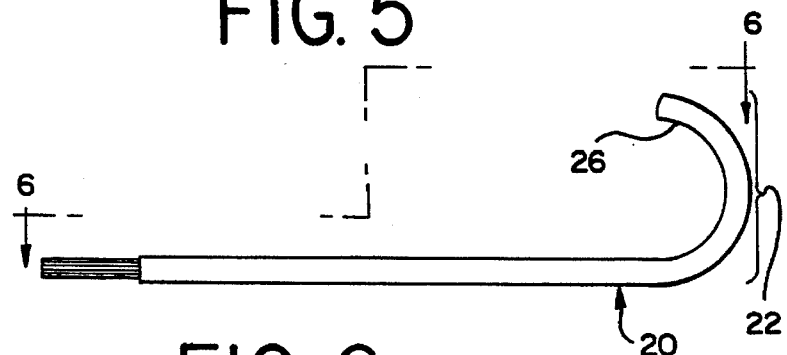
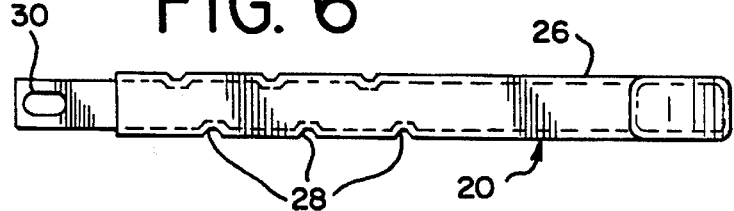
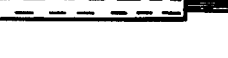
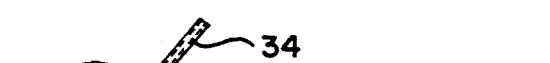
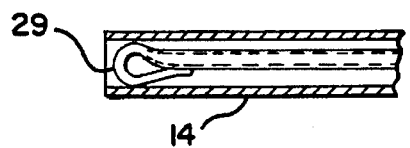

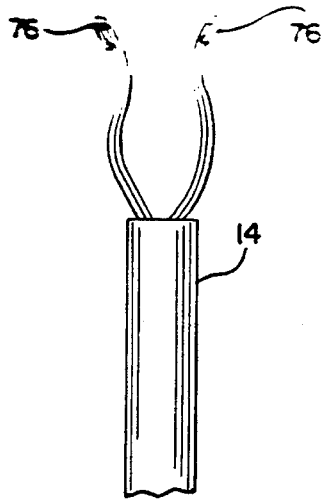
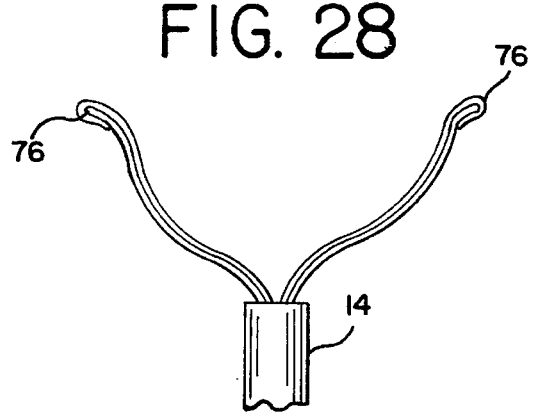
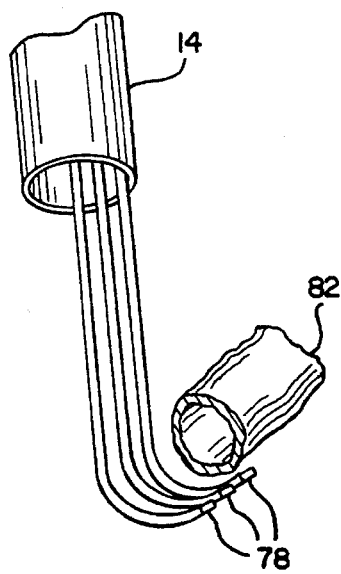
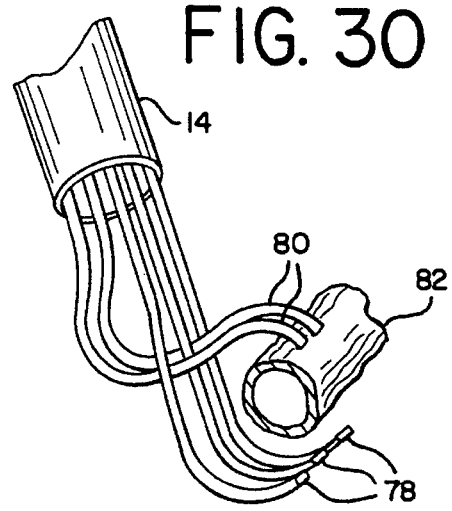
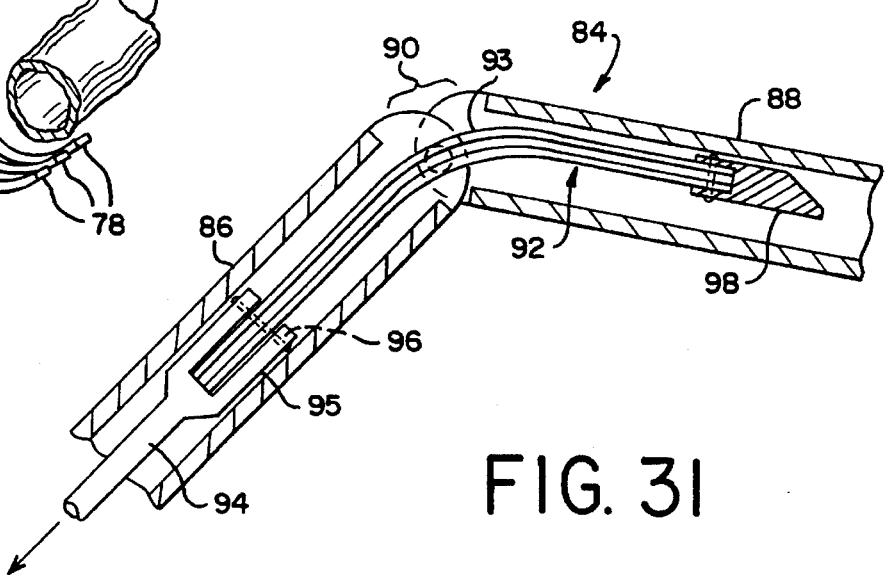

ENDOSCOPIC INSTRUMENT HAVING ARTICULATING ELEMENT

This application is a continuation, of application Ser. No. 08/092,326, filed Jul. 15, 1993, now abandoned.

FIELD OF THE INVENTION

This invention relates generally to surgical instruments; and more particularly, the invention relates to an endoscopic surgical instrument for insertion through a trocar cannula. The endoscopic surgical instrument in accordance with the present invention includes an articulating element which deforms elastically.

BACKGROUND OF THE INVENTION

The burgeoning field of endoscopic surgery has created a demand for a whole new set of articulating endoscopic surgical instruments for insertion through a trocar cannula. These instruments have evolved from similar instruments used in open surgery.

In open surgery, the working sections of retractors and other articulating instruments are made to specific non-linear shapes and sizes to conform to the specific organs or anatomical structures for which they were designed. In endoscopic surgery, these instruments often cannot fit through trocar cannulas. Therefore, a means must be employed wherein a substantially straightened instrument fits through a trocar cannula and articulates to a curvilinear or other non-linear shape after it is extended beyond the end of the cannula. Some prior art endoscopic devices achieve such articulation by means of linked elements in an articulating working section. Other prior art devices achieve such articulation by employing a single, deformable piece which forms at least part of the articulating working section.

The prior art includes variable retractors for endoscopic use wherein a retractable, deformable working section slides in and out of a sheath. When the working section is retracted, it is substantially straightened within the sheath and the sheath is extendable through a trocar cannula. After the sheath is extended through a trocar cannula, the working section is extended from the sheath and assumes a working, curvilinear configuration.

Typically, the deformable working section is a single curved strip which assumes a curved configuration in an unstressed state. The strip is elastically deformable from a curved configuration to a substantially straightened position. It is desirable to be able to bend the working section from a relatively small radius of curvature to a substantially straightened configuration.

The prior art also includes endoscopic instruments wherein an articulating section includes an articulating housing that contains a single, deformable strip. Typically, the strip assumes a substantially straightened configuration in an unstressed state. When the housing is articulated, the strip is elastically deformed to a curved configuration. It is desirable to be able to bend the strip to a relatively small radius of curvature.

The design and construction of an elastically deformable working section is limited by the properties of the materials used. Deformable working sections have been constructed from materials such as nitinol, which is a metal alloy composed of 50 percent nickel and 50 percent titanium and is relatively expensive.

The prior art further includes deformable working sections constructed from shape memory alloys. A description of these alloys and their use in the construction of medical instruments, including endoscopic surgical instruments, is discussed in U.S. Pat. Nos. 4,665,906 and 5,067,957. These shape memory alloys are also relatively expensive.

More conventional materials, such as spring steel, have less elasticity and therefore are less desirable for use in prior art designs of a deformable working section. For example, if desiring a portion or all of the working section to have a radius of curvature of approximately $5/16$ of an inch using a spring temper stainless steel strip, the thickness of the strip is limited to no more than about 0.007 inches, which is the approximate maximum thickness of spring steel that will elastically bend between a straightened configuration and a $5/16$ inch radius of curvature. Unfortunately a 0.007 inch thick strip of steel does not provide much stiffness or resistance to deflection while under load.

By comparison, a strip of nitinol having a thickness of 0.018 inches can elastically bend between a substantially straightened configuration and a $5/16$ inch radius of curvature. The stiffness of a 0.018 inch thick nitinol strip is about five times greater than the stiffness of a 0.007 inch thick spring steel strip.

While using nitinol strengthens a deformable curved working section of an articulating endoscopic surgical instrument, its main drawback is its high cost. It would be desirable to construct the deformable working section from a low cost materials such as spring steel, having properties similar to that of nitinol. It would be desirable to develop variations of surgical instruments employing such a deformable working section to perform a variety of surgical functions.

SUMMARY OF THE INVENTION

The present invention comprises an endoscopic surgical instrument that is extendable through a trocar cannula and has an elastically deformable working section that is constructed from at least two adjacent strips of elastically deformable material.

One embodiment of the surgical instrument in accordance with the invention has an elongated element having a distal end portion and a proximal end portion. The distal end portion is variably movable between a retracted position wherein the distal end portion is inside a sheath and a series of extended positions wherein the distal end portion is outside the sheath. The distal end portion has a deformable working section which is elastically movable from a curved configuration when the working section is outside the sheath to a substantially straightened configuration when the working section is inside the sheath.

The deformable working section has at least two layers or strips which are positioned adjacent each other and constructed so as to cause the working section to be biased towards its curved configuration. The strips are relatively thin and slidably connected to each other so as to permit them to be longitudinally slidable relative to each other in at least one section.

In accordance with a preferred embodiment of the invention, the curved working section is constructed from at least two strips of stainless steel which are elastically bendable from a curved configuration to a substantially straightened configuration. The strips have a thickness in a range of about 0.002 inches to about 0.020 inches, and the number of steel strips is in the range of two to six. The radius of curvature of each strip is in a range of about 0.10 inches to 2.0 inches.

In accordance with a preferred embodiment, the working section has four strips of 301 stainless steel having a thickness of approximately 0.007 inches and having a radius of curvature of approximately 0.25 inches. The working section has a curvature of approximately 180 degrees in the fully extended position. The distal end portion, including the working section, is covered with a shrink wrap plastic tube.

The proximal end portion of the elongated element is a connecting rod that is connected to the curved working section inside the sheath. The connecting rod extends rearwardly from the curved working section and is inserted into a handle that is connected to the proximal end of the sheath.

The handle has a driver mechanism connected to the connecting rod for variably moving the elongated element, including the proximal and distal end portions, between a retracted position and any of a series of extended positions. Preferably the driver mechanism includes a sliding gear rack connected to the connecting rod and a rotatable pinion mechanism which is actuated by a thumbwheel. In an alternative embodiment, the driver mechanism includes a push rod extending rearwardly from the gear rack.

In accordance with alternative embodiments of the invention, the distal end portion of the elongated element may include a paddle, scoop, scalpel, cotton tip, or cautery tip.

In accordance with another alternative embodiment of the invention, the elongated element has multiple distal end portions which separate and form a flared arrangement when in the extended position.

In accordance with another alternative embodiment of the invention, there are multiple elongated elements having one or more distal end portions which are oriented so as to form opposing fingers when in the extended position. Each of the elongated elements is connected to a separate driver mechanism so as to permit each elongated element to be individually and/or sequentially actuated.

In accordance with another embodiment of the invention, an elongated element is contained within an articulating housing. The elongated element has an elastically deformable working section that articulates with the articulating housing.

BRIEF DESCRIPTION OF THE DRAWINGS

A more complete appreciation of this invention, and many of the attendant advantages thereof will be readily apparent as the same becomes better understood by reference to the following detailed description, when considered in conjunction with the accompanying drawings in which like reference numerals indicate the same or similar components, wherein:

FIG. 1 is an elevational view of an endoscopic surgical device constructed in accordance with the invention;

FIG. 2 is a cross-sectional, elevational view of the endoscopic surgical device in accordance with the invention;

FIG. 3 is an elevational view of an elongated element in accordance with the invention;

FIG. 4 is an elevational view of the multiple layers of the distal end portion of the elongated element;

FIG. 5 is an elevational view of the distal end portion wrapped in a plastic tube;

FIG. 6 is a top view of the distal end portion shown in FIG. 5;

FIG. 7 is an elevational view of a distal end portion having a rounded tip;

FIG. 8 is an elevational view of the assembly of strips used to make a distal end portion with a rounded tip as shown in FIG. 7;

FIG. 9 is an elevational view of the strips shown in FIG. 8 after being wrapped in a plastic tube;

FIG. 10 is a partial, cross-sectional view of a distal end portion with a rounded tip that is retracted into a sheath;

FIG. 27 is a partial elevational view of an alternative embodiment of the invention having two opposed distal end portions;

FIG. 28 is an elevational view of the two opposed distal end portions in FIG. 27 wherein the distal end portions are fully separated;

FIG. 29 is a perspective view of an alternative embodiment of the invention which includes two elongated elements wherein one of the elongated elements having three fingers is extended from the sheath and around an internal organ;

FIG. 30 is a perspective view of the embodiment shown in FIG. 29 wherein a second elongated element having two fingers is extended from the sheath and around the other side of the internal organ; and FIG. 31 is a partial cross-sectional view of an alternative embodiment of the invention which includes a housing with an articulating joint and an elongated deformable element contained therein.

DETAILED DESCRIPTION OF THE INVENTION

Figure 11:
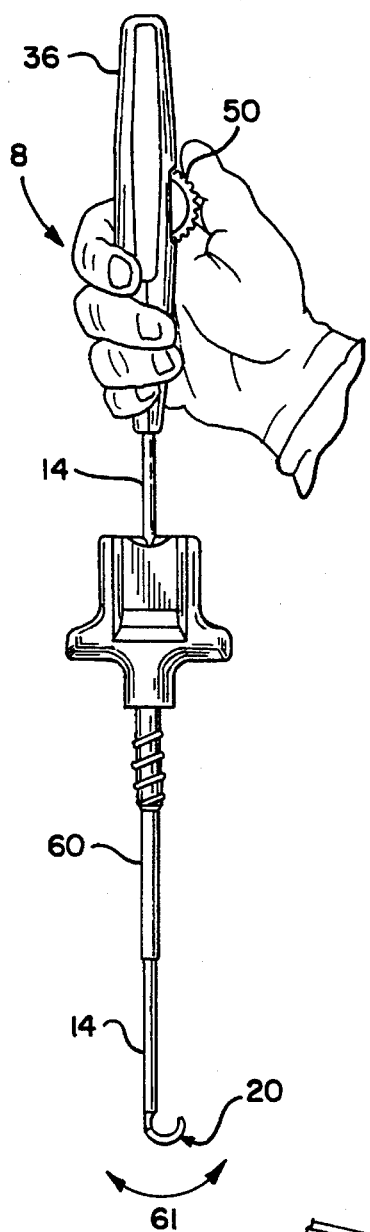
FIG. 11 is an elevational view of an endoscopic surgical instrument in accordance with the invention that is extended through a trocar cannula wherein the distal end portion is extended into its curved configuration.

The following is a detailed description of the invention. The detailed description is not intended to be an exhaustive description of all embodiments within the scope of the invention and is not intended to limit the scope of the claims to the disclosed embodiments. Other embodiments within the scope of the claims will be apparent to those skilled in the art.

Referring to FIGS. 1 and 2, the endoscopic surgical instrument of this invention 8 has two basic portions: an endoscopic portion 10 and a handle portion 12. The endoscopic portion includes a sheath 14 that encloses an elongated element, as described in detail below, which is longitudinally slidable within the sheath 14. Preferably, the sheath 14 is stainless steel and has a steel spacer or tongue 15 affixed inside of the distal end of the sheath 14.

Referring to FIG. 3, the elongated element 16 is an assembly comprising a proximal end portion 18 and distal end portion 20 that are connected by a pin connection 19. The proximal end portion 18 is preferably a stainless steel rod. The distal end portion 20 defines a curved working section 22.

Referring to FIG. 4, the working section 22 has at least two curved layers or strips 24 which are positioned adjacent each other. The strips 24 are relatively thin and slidably connected to each other so as to permit them to be longitudinally slidable relative to each other.

Preferably, the strips 24 of the distal end portion 20 are constructed from stainless steel having a thickness in the range of about 0.002 inches to about 0.020 inches. There are preferably four strips in the curved working section 22, each constructed from fully hardened 301 stainless steel which is about 0.007 inches thick.

Also, there may be a fifth strip 26 (FIG. 4) in the straight section of the distal end portion 20 to add rigidity. The fifth strip is preferably constructed from fully hardened 301 stainless steel which is somewhat thicker than the other strips. Other comparable materials that are suitable for surgical use, having similar bending and strength characteristics and having similar dimensions, may also be used.

The strips 24 are constructed so as to be biased toward a curved configuration (FIG. 4). The radius of curvature of the working section 22 is in the range of from about 0.10 inches to about 1.5 inches. The radius of curvature is preferably about 0.25 inches.

The multiple strips 24 of the working section 22 are slidably connected to each other so that during bending and straightening of the working section 22 the individual strips 24 bend individually and slide relative to each other rather than bending as a monolithic unit. This bending and sliding of the individual strips enhances elastic bending of the working section as a whole between its curved configuration and a substantially straightened configuration. Elastic bending refers to bending without yielding.

Referring to FIG. 5, the curved strips 24 of the distal end portion 20 are slidably connected to each other with a plastic tube 26. The plastic tube 26 permits the enclosed strips to slide relative to each during the bending and straightening of the curved working section 22. Preferably, the plastic tube 26 is a tubing sold under the trademark KYNAR® by Raychem Corporation.

The plastic tubing 26 is slipped over the distal end portion 20, cut off slightly beyond the distal tip, and then shrunk with an application of heat. Referring to FIG. 6, the tubing 26 is preferably engaged by a series of notches 28 in a straight section of the distal end portion 20 so as to minimize slippage of the strips 24 relative to each other in the straight section while permitting such slippage in the curved working section 22.

Using a plastic tube 26 to cover the distal end portion 20 has the advantage of providing a soft touch when the working section 22 of the distal end portion 20 comes into contact with delicate internal organs. Thus, the danger of trauma is reduced.

The plastic tubing also has the advantage of providing a smooth surface to minimize friction between the distal end portion 20 and the sheath 14 when the distal end portion is being moved into or out of the sheath.

It is preferable to provide an elongated hole 30 in the distal end portion 20 (FIG. 6) for receiving a pin 19 that is inserted through the hole 30 and connecting the distal end portion 20 and the proximal end portion 18 of the elongated element 16 (FIG. 3). This permits the longitudinal movement of the strips 24 relative to each other when the strips bend.

In an alternative embodiment (not illustrated), the strips of the distal end portion may be rigidly connected at only one point located in, or adjacent to, the curved working section by brazing, welding, etc. A rigid connection at only one point permits the strips to slide relative to each other at all other locations as they are moved between a curved configuration and substantially straightened configuration.

Referring to FIG. 7, in an alternative embodiment, the tip 29 of the distal end portion 20 is looped. Referring to FIG. 8, the loop is constructed from three strips 31 which are stacked on the outside of a fourth strip having an extended tip 32. A fifth reinforcing straight strip 33 runs along the bottom of the stacked strips. The entire stack of strips is wrapped with a plastic tubing 34 as shown in FIG. 9. Then the tip is bent around to form the loop 29 as shown in FIG. 7. As seen in FIG. 10, the width of the loop 29 is less than the inside diameter of the sheath 14 so that the loop can be fully withdrawn inside the sheath.

The loop construction of the tip 29 of the distal end portion 20 has the advantage of providing a rounder, more blunt tip which is less likely to cause inadvertent trauma when it is inserted into a body cavity. Further, the open end of the plastic tubing 34 is turned inwardly and away from tissue in the body cavity where it might contact and collect unwanted tissue.

Referring to FIGS. 1 and 2, the handle portion 12 includes a handle 36 that is connected to the proximal end of the sheath 14. In accordance with a preferred embodiment, the handle 36 is molded plastic and has recesses to hold and retain a flange 38 or other protrusion on the sheath (FIG. 2) so as to rigidly connect the sheath to the handle.

Referring to FIG. 2, the rod 18 extends proximally into the interior of the handle 36 wherein it is connected to a gear rack 44 through a pin connection 42. Preferable, the gear rack 44 is molded plastic. The rod 18 and gear rack 44 assembly slide longitudinally as a single unit within the handle 36.

The gear rack 44 engages a pinion gear 48 which is connected to a thumbwheel 50. The pinion 48 is preferably plastic and is molded integral with one of the two halves of the plastic thumbwheel 50 and rigidly attached to the other half. The pinion 48 is located between the two halves of the thumbwheel 50 and acts as a spacer separating them.

An axle pin 52 extends outwardly from each side of the thumbwheel 50 and is held and retained by corresponding holes (not shown) in the interior of the handle 36. Thus, the pinion 48 and thumbwheel 50 are rotatably connected to the handle so as to permit rotation of the pinion and thumbwheel relative to the handle.

The gear rack 44 extends rearwardly between the two halves of the thumbwheel 50 as it engages the pinion 48. When the thumbwheel and pinion are rotated, the pinion drives the gear rack in a longitudinal direction (forwardly or rearwardly depending upon the direction of rotation of the thumbwheel and pinion). Thus, the thumbwheel, pinion and gear rack operate as a driver mechanism for moving the rod 18 in a longitudinal direction.

A detent mechanism may be provided for restricting rotation of the thumbwheel 50 and thereby controlling incremental longitudinal movement of the thumbwheel 50 and driver mechanism. Referring to FIG. 2, the detent mechanism consists of a plastic strip 58 or "clicker" affixed to the handle 36 and extending into corresponding notches on the exterior of the thumbwheel 50. The clicker 58 rides in the notches of the thumbwheel 50 and thus acts as a ratchet-type mechanism. Preferably, the restriction against distal movement of the gear rack 44 is greater than the restriction against proximal movement.

Movement of the gear rack 44 in the proximal direction is limited by a stop pin 59. (FIG. 2). Movement in the distal direction is limited by a shoulder 45 against which the distal end of the gear rack 44 makes contact.

In an alternative embodiment, the driver mechanism also includes a push rod 54 which is rigidly connected to the rear end of the gear rack 44, as shown in phantom lines in FIG. 2. The push rod 54 extends rearwardly from the gear rack through a hole in the rear end of the handle 36. Preferably, the push rod 54 is plastic. The push rod 54 may be used for gross adjustments of the driver mechanism, or when heavier loads are anticipated.

Referring to FIG. 11, the endoscopic surgical instrument of this invention 8 is designed to function as a variable retractor that is extendable through a trocar cannula 60. In order to insert the instrument into a trocar cannula 60, the distal end portion 20, must be retracted into the sheath 14 to avoid interference as the sheath 14 is inserted into the trocar cannula 60.

When the distal end portion 20 is retracted into the sheath 14, the working section 22 is straightened from its unstressed curved configuration to a substantially straightened configuration. Since the working section 22 comprises strips 24 (FIG. 4), each strip 24 will bend independently and slide relative to one another as the working section 22 is straightened. This separate and independent bending of the various strips 24 permits the working section 22 to have more resilience than a comparable monolithic construction of the same total thickness. As a result of this resilience, the working section 22 may be substantially straightened from a curved configuration having a much smaller radius of curvature than would be possible in a comparable monolithic structure of the same material and dimensions.

During usage as a retractor, the distal end portion 20, with its layered construction, has a sufficient amount of "give" in order to avoid trauma when the surgical instrument is inadvertently moved or jostled.

After the distal end portion 20 is fully retracted into the sheath 14, the sheath 14 is inserted into the trocar cannula 60 and pushed through the cannula until it emerges from the end of the cannula inside a body cavity (FIG. 11). Then, the distal end portion 20 is moved distally to its extended position. As the distal end portion 20 emerges, it travels around its original radius of curvature as indicated by the arrow 61. Preferably, the distal end portion 20 extends and curves to form a "J" configuration.

Figure 12:
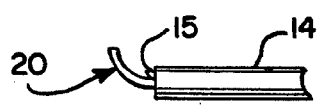
FIG. 12 is a partial view of the working section of a distal end portion extended approximately 90 degrees from a sheath.

The amount of extension of the distal end portion 20 can be varied by adjustment of the thumbwheel 50 and then held by the detent mechanism 58. Partial extension is shown in FIG. 12.

In order to remove the surgical instrument from the trocar cannula 60 (FIG. 11), the distal end portion 20 is retracted into the sheath 14. During this retraction, the working section 22 is moved from a curved configuration to the straightened configuration within the sheath 14. Then the sheath is pulled out of the trocar cannula 60.

Figure 14:
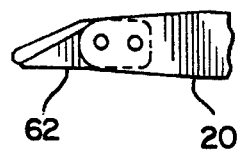
FIG. 14 is a view of the scalpel shown in FIG. 13 along the line 14—14.
Figure 13:
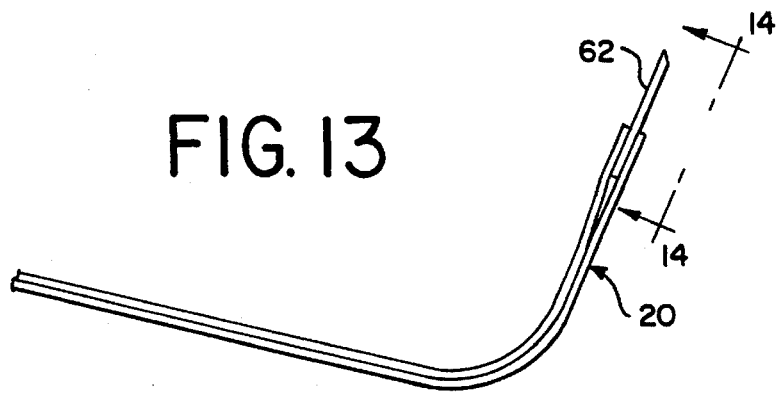
FIG. 13 is an elevation view of a scalpel attached to a distal end portion.
Figure 15:
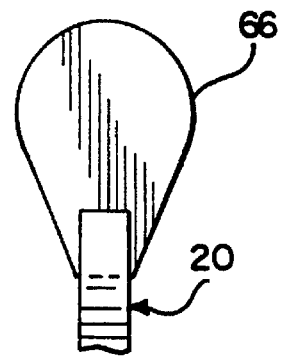
FIG. 15 is an enlarged plan view of a paddle attached to a distal end portion.
Figure 16:
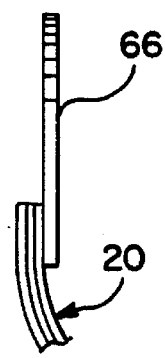
FIG. 16 is a side view of the paddle shown in FIG. 15.
Figure 17:
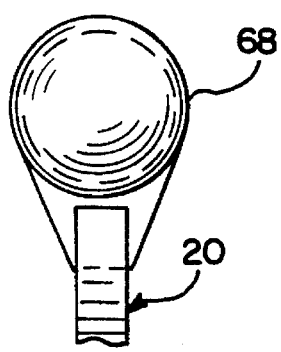
FIG. 17 is an enlarged plan view of a scoop attached to a distal end portion.
Figure 18:
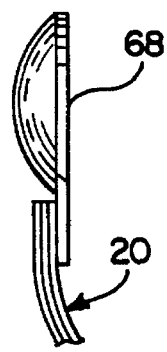
FIG. 18 is a side view of the scoop shown in FIG. 17.
Figure 19:
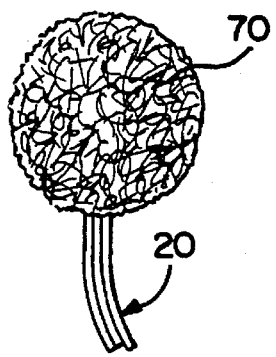
FIG. 19 is an enlarged side view of cotton tip on a distal end portion.

Alternative embodiments of the present invention include various tools attached to the working section of the distal end portion 20, including a scalpel 62 (FIGS. 13 and 14), a paddle 66 (FIGS. 15 and 16), a scoop 68 (FIGS. 17 and 18), and a cotton-tipped dissector 70 (FIG. 19). The attachment of various other tools to the distal end portion will be apparent to one skilled in the art.

Figure 20:
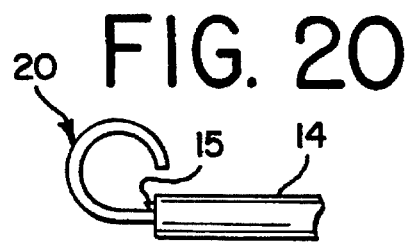
FIG. 20 is a partial view of the working section of a distal end portion extended approximately 270 degrees from a sheath.

The curvature of the distal end portion 20 may extend to any desired angle. For example the curvature of the working section may extend to 180 degrees (FIG. 1), 70 degrees (FIG. 13) or 270 degrees (FIG. 20). In the preferred embodiment, the curvature extends to approximately 180 degrees.

Figure 21:
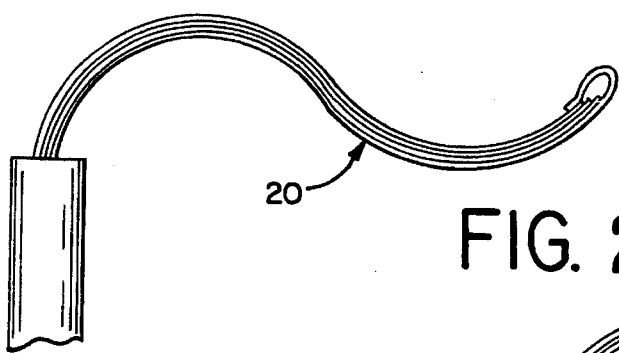
FIG. 21 is a partial elevational view of an alternative embodiment of the invention having an S-shaped distal end portion.
Figure 22:
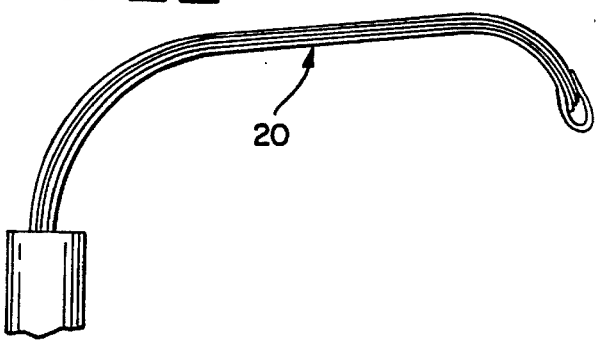
FIG. 22 is a partial elevational view of an alternative embodiment of the invention having a distal end portion with multiple curves in the same direction.
Figure 23:
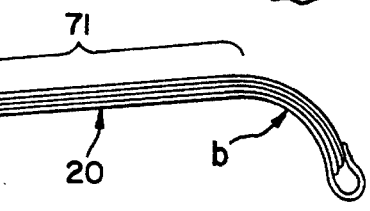
FIG. 23 is a partial elevational view of an alternative embodiment of the invention having a distal end portion with multiple curves in the same direction, each curve having a different radii of curvature.
Figure 24:
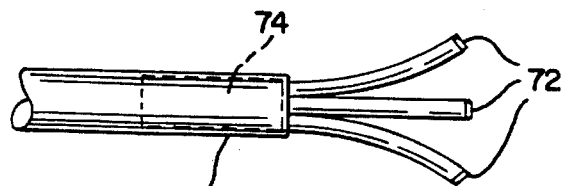
FIG. 24 is a plan view of a three-fingered distal end portion extending from a sheath.

Further, the distal end portion 20 may be S-shaped (FIG. 21) or it may have multiple curves in the same direction (FIG. 22). As shown in FIG. 23, the curves may have different radii of curvature as indicated by the arrows a and b, and may have a straight section 71. Also, the length of the strips on a single distal end portion 20 may vary in order to vary the stiffness of the curved working section along its length (FIG. 23).

In an alternative aspect of the invention as shown in FIGS. 24–30, there may be multiple distal end portions, each having the multi-layer construction discussed above. In one alternative embodiment (FIGS. 24 and 25), three separate distal end portions 72 are in a flared arrangement when in the extended position. Their proximal ends are connected to each other at their connection to the rod.

Figure 26:
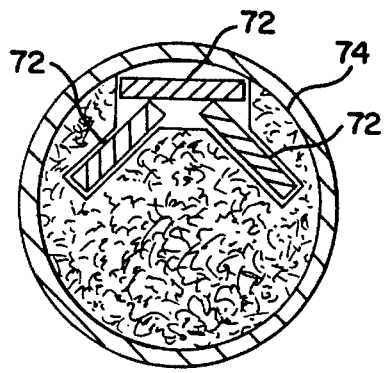
FIG. 26 is a cross-sectional view taken along the line 26—26 in FIG. 25.
Figure 25:
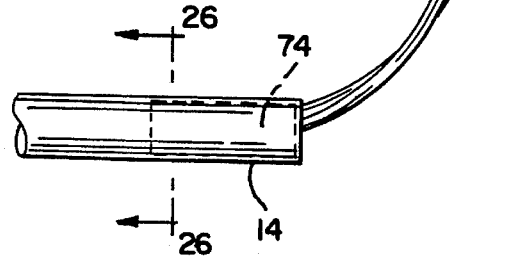
FIG. 25 is an elevational view of the three fingered distal end portion shown in FIG. 24.

In order to form a flared arrangement, the distal end portions 72 pass through an apertured plug 74 located inside the sheath 14 as shown in FIG. 26. The apertured plug 74 is configured to separate the distal end portions 72 and direct them into the flared arrangement. Preferably, the apertured plug is molded plastic.

In another alternative embodiment, referring to FIGS. 27 and 28, there are two opposed distal end portions 76. As the distal end portions 76 are extended from the sheath 14, they move from a partially separated position (FIG. 27) to a fully separated position (FIG. 28). In use in surgery, the distal end portions 76 may be used as a spreader retractor to open lumens or otherwise separate tissue.

Referring to FIGS. 29 and 30, in an alternative aspect of the invention, there are multiple elongated elements within a single sheath 14, each elongated element being actuated by a separate driver mechanism (not illustrated). The distal end portions of the elongated elements are oriented to form an opposing set of fingers or hands 78 and 80 as shown in FIG. 30.

The opposing sets of fingers 78 and 80 are extended one at a time. The first set of fingers 78 is extended to reach behind an anatomical part 82 to be grasped as shown in FIG. 29. Thereafter, the second set of fingers 80 is extended to grasp the anatomical part 82 as shown in FIG. 30.

In an alternative embodiment of the invention shown in FIG. 31, an articulating housing 84 of an endoscopic surgical instrument has two housing portions 86 and 88 connected with an articulating joint 90. An elongated, deformable element 92 is contained within the housing. The elongated element 92 includes a working section 93 comprising a plurality of strips of the same construction as that of the strips used in the embodiments discussed above. The strips may be biased toward either a curved configuration or a substantially straightened configuration. The elongated element 92 is elastically bendable from its initial unstressed configuration. Therefore, the elongated element 92 articulates with the articulating housing 84 and is elastically bendable between a curved configuration and a less curved or straightened configuration.

The elongated element 92 is connected to a drive rod 94 through a clevis mechanism 95 with a pin 96 received in an elongated hole in the elongated element 92, similar to the elongated hole 30 shown in FIG. 6.

At the distal tip of the elongated element 92 there is an end element or a working tool 98. In FIG. 31, the end element is shown as a wedge-like structure 98. Preferably, the elongated element 92 is slidable with the clevis mechanism 95 and end element 98 within said housing 84 between a retracted position as shown in FIG. 31 and an extended position (not illustrated).

Various types of end elements 98 could be employed to actuate, or otherwise engage, end effector mechanisms (e.g., such as might be used in staplers, ligating clip appliers, clamping jaws, etc.). Alternatively, the various end element working tools described herein (retractor, scalpel, paddle, scoop, cotton tip, fingers, etc.), or other suitable tools, may be used to directly contact and manipulate tissue.

From the foregoing, it will be observed that numerous variations and modifications may be effected without departing from the spirit and scope of the invention. It is to be understood that no limitation with respect to the specific apparatus illustrated herein in intended or should be inferred. All such variations and modifications are intended to be covered by the appended claims.

What is claimed is:

1. An endoscopic surgical instrument for insertion by a user through a trocar cannula, comprising:

a sheath, said sheath having a proximal end proximal to the user of said instrument, and an opposite distal end; at least one elongated element positioned inside said sheath; said elongated element having a distal end portion which is movable between a retracted position wherein said distal end portion is inside said sheath and an extended position wherein said distal end portion is outside of said distal end of said sheath; said distal end portion having a working section, said sheath engaging said working section wherein said working section is elastically moved from a curved configuration when said working section is outside of said sheath to a substantially straightened configuration when said working section is inside said sheath; said working section including a least two flat strips which are positioned adjacent each other and individually constructed with said curved configuration so as to cause said working section to be permanently biased towards said curved configuration, said curved configuration having a predetermined radius of curvature said strips being generally parallel to each other when said working section is in said curved configuration; each of said strips having a distal end located in said working section and a proximal end located proximally of said distal end; said strips being relatively thin and being affixed to each other at said proximal ends so as to be non-slidable relative to each other at said proximal ends and longitudinally slidable relative to each other at said distal ends.

2. An endoscopic surgical instrument in accordance with claim 1 wherein the number of said strips in said working section is in the range of from about two to about six.

3. An endoscopic surgical instrument in accordance with claim 2 having four of said strips in said working section.

4. An endoscopic surgical instrument in accordance with claim 1 wherein said distal end portion includes a stiffener strip.

5. An endoscopic surgical instrument in accordance with claim 1 wherein the radius of curvature of said working section of said distal end portion is in the range from about 0.10 inches to about 1.5 inches.

6. An endoscopic surgical instrument in accordance with claim 1 wherein the radius of curvature of said working section of said distal end portion is about 0.25 inches.

7. An endoscopic surgical instrument for insertion by a user through a trocar cannula, comprising:

a housing, said housing having a proximal end proximal the user of said instrument and an opposite distal end; and at least one elongated element extending at least partially within said housing and being longitudinally movable between a retracted position and an extended position; and said element having a working section which is elastically bendable from a curved configuration and which includes at least two relatively thin flat strips which are positioned adjacent each other; each of said strips having a distal end located in said working section and a proximal end located proximally of said working section; said element being simultaneously bendable and longitudinally movable; said distal end of said housing engaging said working section wherein said element is substantially straightened from said curved configuration as said element moves longitudinally from said extended position to said retracted position; said strips being generally parallel to each other when said working section is in said curved configuration; said strips being affixed to each other at said proximal ends so as to be non-slidable relative to each other at said proximal ends and longitudinally slidable relative to each other at said distal ends and being individually constructed with said curved configuration in said working section.

8. An endoscopic surgical instrument for insertion by a user through a trocar cannula, comprising:

a sheath, said sheath having a proximal end proximal the user of said instrument, and an opposite distal end; at least one elongated element positioned inside said sheath, said elongated element having a proximal end portion and a distal end portion; said elongated element being movable between a retracted position wherein said distal end portion is inside said sheath and an extended position wherein said distal end portion is outside of said sheath; said distal end portion having a working section, said sheath engaging said working section wherein said working section is elastically moved from a curved configuration when said working section is outside of said sheath to a substantially straightened configuration when said working section is inside said sheath by engagement of said sheath with said working section; said working section including at least two flat strips which are positioned adjacent each other and individually constructed with said curved configuration so as to cause said working section to be permanently biased towards said curved configuration, said curved configuration having a predetermined radius of curvature; said strips being generally parallel to each other when said working section is in said curved configuration; each of said strips having a distal end located in said working section and a proximal end located proximally of said working section; said strips being relatively thin and being affixed to each other at said proximal ends so as to be non-slidable relative to each other at said proximal ends and longitudinally slidable relative to each other at said distal ends.

9. An endoscopic surgical instrument in accordance with claim 8 wherein each of said strips of said working section is formed of spring steel.

10. An endoscopic surgical instrument in accordance with claim 9 wherein each of said strips of said working section is formed of 301 stainless steel.

11. An endoscopic surgical instrument in accordance with claim 9 wherein each of said strips has a thickness in a range of about 0.002 inches to about 0.020 inches.

12. An endoscopic surgical instrument in accordance with claim 9 wherein each of said strips is approximately 0.007 inches thick.

13. An endoscopic surgical instrument in accordance with claim 8 wherein the number of said strips in said working section is in the range of from about two to about six.

14. An endoscopic surgical instrument in accordance with claim 13 having four of said strips in said working section.

15. An endoscopic surgical instrument in accordance with claim 8 wherein said distal end portion includes a stiffener strip.

16. An endoscopic surgical instrument in accordance with claim 15 wherein said stiffener strip is formed of spring steel having a thickness of approximately 0.040 inches.

17. An endoscopic surgical instrument in accordance with claim 8 wherein the radius of curvature of said working section of said distal end portion is in the range from about 0.10 inches to about 1.5 inches.

18. An endoscopic surgical instrument in accordance with claim 8 wherein the radius of curvature of said working section of said distal end portion is about 0.25 inches.

19. An endoscopic surgical instrument in accordance with claim 8 wherein said strips are covered with a plastic material.

20. An endoscopic surgical instrument in accordance with claim 19 wherein said plastic material is formed from plastic tubing.

21. An endoscopic surgical instrument in accordance with claim 8 wherein the proximal end of said sheath is attached to a handle and the proximal end portion of said elongated element is slidably inserted into said handle; said handle having a driver mechanism for moving said elongated element between said retracted position and said extended position.

22. An endoscopic surgical instrument in accordance with claim 21 wherein said elongated element is connected to a longitudinally extending gear rack and said driver mechanism includes a thumbwheel and pinion for engaging and moving said gear rack in a longitudinal direction.

23. An endoscopic surgical instrument in accordance with claim 22 wherein said driver mechanism includes a push rod which is rigidly connected to said gear rack, said push rod extending proximally from said gear rack and said handle.

24. An endoscopic surgical instrument in accordance with claim 22 wherein said thumbwheel is engaged by a detent means for providing incremental rotation of said thumbwheel.

25. An endoscopic surgical instrument in accordance with claim 8 wherein said distal end portion includes a cautery tip.

26. An endoscopic surgical instrument in accordance with claim 8 wherein said distal end portion includes a scalpel.

27. An endoscopic surgical instrument in accordance with claim 8 wherein said distal end portion includes a paddle.

28. An endoscopic surgical instrument in accordance with claim 8 wherein said distal end portion includes a scoop.

29. An endoscopic surgical instrument in accordance with claim 8 wherein said distal end portion includes a dissector tip.

30. An endoscopic surgical instrument in accordance with claim 8 wherein said elongated element has a plurality of distal end portions.

31. An endoscopic surgical element in accordance with claim 30 wherein said distal end portions are in a flared arrangement when in said extended position.

32. An endoscopic surgical instrument in accordance with claim 31 having an apertured plug for separating said distal end portions and directing them into said flared arrangement.

33. An endoscopic surgical instrument in accordance with claim 30 wherein said distal end portions are movable from a closed position when inside said sheath to a separated position when extended from said sheath.

34. An endoscopic surgical instrument in accordance with claim 33 wherein said distal end portions are variably movable from said closed position to said separated position.

35. An endoscopic surgical instrument in accordance with claim 8 having multiple elongated elements.

36. An endoscopic surgical instrument in accordance with claim 35 wherein the distal end portions of said elongated elements are oriented so as to form opposing fingers when in said extended position.

37. An endoscopic surgical instrument in accordance with claim 35 wherein each of said elongated elements has multiple distal end portions.

38. An endoscopic surgical element in accordance with claim 35 wherein each of said elongated elements is connected to a separate driver mechanism so as to permit each elongated element to be individually actuated.

39. An endoscopic instrument in accordance with claim 8 wherein said curved configuration of said working section includes multiple curves.

40. An endoscopic surgical instrument in accordance with claim 39 wherein said multiple curves have different radii of curvature.

41. An endoscopic surgical instrument in accordance with claim 39 wherein said curves are separated by a straight portion.

42. An endoscopic surgical instrument in accordance with claim 8 wherein said working section is S-shaped.

43. An endoscopic surgical instrument in accordance with claim 8 wherein said strips have different lengths.

44. An endoscopic surgical instrument in accordance with claim 8 wherein the distal tip of said distal end portion is rounded.

45. An endoscopic surgical instrument in accordance with claim 8 wherein one of said strips extends beyond the distal ends of the other strips and is bent around said other strips.

46. An endoscopic surgical element in accordance with claim 8 wherein said distal end portion is variably movable between said retracted position and said extended position.

* * * * *